US010952889B2

(12) United States Patent
Newton et al.

(10) Patent No.: US 10,952,889 B2
(45) Date of Patent: Mar. 23, 2021

(54) USING WICKING MATERIAL TO COLLECT LIQUID FOR TRANSPORT

(71) Applicant: PureWick Corporation, El Cajon, CA (US)

(72) Inventors: Raymond John Newton, Bonsall, CA (US); Joseph Mark Forehand, La Mesa, CA (US)

(73) Assignee: PUREWICK CORPORATION, El Cajon, CA (US)

( * ) Notice: Subject to any disclaimer, the term of this patent is extended or adjusted under 35 U.S.C. 154(b) by 320 days.

(21) Appl. No.: 15/171,968

(22) Filed: Jun. 2, 2016

(65) Prior Publication Data

US 2017/0348139 A1    Dec. 7, 2017

(51) Int. Cl.
*A61F 5/44*    (2006.01)
(52) U.S. Cl.
CPC .............. *A61F 5/4404* (2013.01); *A61F 5/44* (2013.01); *A61F 5/4401* (2013.01)
(58) Field of Classification Search
CPC ........ A61F 5/44; A61F 5/4401; A61F 5/4402; A61F 5/4404
See application file for complete search history.

(56) References Cited

U.S. PATENT DOCUMENTS

| 1,742,080 A | 12/1929 | Jones |
| 2,644,234 A | 7/1953 | Earl |
| 2,968,046 A | 1/1961 | Duke |
| 3,087,938 A | 4/1963 | Reimann et al. |
| 3,198,994 A | 8/1965 | Hildebrandt et al. |
| 3,312,981 A | 4/1967 | McGuire et al. |

(Continued)

FOREIGN PATENT DOCUMENTS

| CN | 1533755 A | 10/2004 |
| CN | 1602825 A | 4/2005 |

(Continued)

OTHER PUBLICATIONS

International Search Report and Written Opinion for International Application No. PCT/US16/49274, dated Dec. 1, 2016, 12 pages.

(Continued)

*Primary Examiner* — Kai H Weng
(74) *Attorney, Agent, or Firm* — Dorsey & Whitney LLP

(57) ABSTRACT

A container for collecting liquid for transport, includes a shell having a port adapted for receiving tubing and configured to define a chamber that has a window in an exterior surface of the shell. The window is so positioned that when a wicking material, which is adapted to be applied against a particular source of moisture and which is so dimensioned that when the wicking material is received within the shell and applied through the window to the particular source of moisture, the shell is at least partially closed so that when tubing is inserted through the port into the shell chamber and the shell is otherwise closed a partial vacuum can be created within the shell chamber to draw moisture into the shell chamber through the wicking material for collection as a liquid within the shell chamber for transport from the shell chamber via the tubing. A wicking material applicator includes a material having openings and formed to define an extended hollow framework about which the wicking material can be, or is, disposed.

17 Claims, 1 Drawing Sheet

(56) References Cited

U.S. PATENT DOCUMENTS

| | | |
|---|---|---|
| 3,349,768 A | 10/1967 | Keane |
| 3,366,116 A | 1/1968 | Huck |
| 3,400,717 A | 9/1968 | Cubitt et al. |
| 3,406,688 A | 10/1968 | Cubitt R |
| 3,511,241 A | 5/1970 | Lee |
| 3,512,185 A | 5/1970 | Ellis |
| 3,520,300 A | 7/1970 | Flower |
| 3,613,123 A | 10/1971 | Langstrom |
| 3,651,810 A | 3/1972 | Ormerod |
| 3,726,277 A | 4/1973 | Hirschman |
| 4,020,843 A | 5/1977 | Kanall |
| 4,022,213 A | 5/1977 | Stein |
| 4,200,102 A | 4/1980 | Duhamel et al. |
| 4,202,058 A | 5/1980 | Anderson |
| 4,233,025 A | 11/1980 | Larson et al. |
| 4,246,901 A | 1/1981 | Frosch et al. |
| 4,257,418 A | 3/1981 | Hessner |
| 4,270,539 A | 6/1981 | Frosch et al. |
| 4,352,356 A | 10/1982 | Tong |
| 4,387,726 A | 6/1983 | Denard |
| 4,425,130 A | 1/1984 | Desmarais |
| 4,453,938 A | 6/1984 | Brendling |
| 4,457,314 A | 7/1984 | Knowles |
| 4,526,688 A | 7/1985 | Schmidt, Jr. et al. |
| 4,528,703 A | 7/1985 | Kraus |
| 4,581,026 A | 4/1986 | Schneider |
| 4,610,675 A | 9/1986 | Triunfol |
| 4,627,846 A | 12/1986 | Ternstroem |
| 4,631,061 A | 12/1986 | Martin |
| 4,650,477 A | 3/1987 | Johnson |
| 4,692,160 A | 9/1987 | Nussbaumer |
| 4,713,066 A | 12/1987 | Komis |
| 4,747,166 A | 5/1988 | Kuntz |
| 4,752,944 A | 6/1988 | Conrads et al. |
| 4,769,215 A | 9/1988 | Ehrenkranz |
| 4,772,280 A | 9/1988 | Rooyakkers |
| 4,790,835 A | 12/1988 | Elias |
| 4,791,686 A | 12/1988 | Taniguchi et al. |
| 4,795,449 A | 1/1989 | Schneider et al. |
| 4,799,928 A | 1/1989 | Crowley, IV |
| 4,804,377 A | 2/1989 | Hanifl et al. |
| 4,820,297 A | 4/1989 | Kaufman et al. |
| 4,846,909 A | 7/1989 | Klug et al. |
| 4,882,794 A | 11/1989 | Stewart |
| 4,883,465 A | 11/1989 | Brennan |
| 4,886,508 A | 12/1989 | Washington |
| 4,886,509 A | 12/1989 | Mattsson |
| 4,889,533 A | 12/1989 | Beecher |
| 4,905,692 A | 3/1990 | More |
| 4,965,460 A | 10/1990 | Tanaka et al. |
| 5,002,541 A | 3/1991 | Conkling et al. |
| 5,004,463 A | 4/1991 | Nigay |
| 5,031,248 A | 7/1991 | Kemper |
| 5,049,144 A | 9/1991 | Payton |
| 5,071,347 A | 12/1991 | McGuire |
| 5,084,037 A | 1/1992 | Barnett |
| 5,100,396 A | 3/1992 | Zamierowski |
| 5,147,301 A | 9/1992 | Ruvio |
| 5,195,997 A | 3/1993 | Carns |
| 5,203,699 A | 4/1993 | McGuire |
| 5,244,458 A | 9/1993 | Takasu |
| 5,294,983 A | 3/1994 | Ersoz et al. |
| 5,295,983 A | 3/1994 | Kubo |
| 5,300,052 A | 4/1994 | Kubo |
| 5,382,244 A | 1/1995 | Telang |
| 5,466,229 A | 11/1995 | Elson et al. |
| 5,478,334 A | 12/1995 | Bernstein |
| 5,499,977 A | 3/1996 | Marx |
| D373,928 S | 9/1996 | Green |
| 5,618,277 A | 4/1997 | Goulter |
| 5,628,735 A | 5/1997 | Skow |
| 5,636,643 A | 6/1997 | Argenta et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,752,944 A | 5/1998 | Dann et al. |
| 5,772,644 A | 6/1998 | Bark et al. |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,887,291 A | 3/1999 | Bellizzi |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,972,505 A | 10/1999 | Phillips et al. |
| 6,059,762 A | 5/2000 | Boyer et al. |
| 6,063,064 A | 5/2000 | Tuckey et al. |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,177,606 B1 | 1/2001 | Etheredge et al. |
| 6,209,142 B1 | 4/2001 | Mattsson et al. |
| 6,248,096 B1 | 6/2001 | Dwork et al. |
| 6,311,339 B1 | 11/2001 | Kraus |
| 6,336,919 B1 | 1/2002 | Davis et al. |
| 6,338,729 B1 | 1/2002 | Wada et al. |
| 6,409,712 B1 | 6/2002 | Dutari et al. |
| 6,416,500 B1 | 7/2002 | Wada et al. |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,540,729 B1 | 4/2003 | Wada et al. |
| 6,547,771 B2 | 4/2003 | Robertson et al. |
| 6,569,133 B2 | 5/2003 | Cheng et al. |
| 6,592,560 B2 | 7/2003 | Snyder et al. |
| 6,620,142 B1 | 9/2003 | Flueckiger |
| 6,635,038 B2 | 10/2003 | Scovel |
| 6,685,684 B1 | 2/2004 | Falconer |
| 6,702,793 B1 | 3/2004 | Sweetser et al. |
| 6,706,027 B2 | 3/2004 | Harvie |
| 6,732,384 B2 | 5/2004 | Scott |
| 6,740,066 B2 | 5/2004 | Wolff et al. |
| 6,783,519 B2 | 8/2004 | Samuelsson |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,912,737 B2 | 7/2005 | Ernest et al. |
| 6,918,899 B2 | 7/2005 | Harvie |
| 6,979,324 B2 | 12/2005 | Byordi et al. |
| 7,018,366 B2 | 3/2006 | Easter |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,220,250 B2 | 5/2007 | Suzuki et al. |
| 7,335,189 B2 | 2/2008 | Harvie |
| 7,358,282 B2 | 4/2008 | Krueger et al. |
| 7,390,320 B2 | 6/2008 | MacHida et al. |
| 7,488,310 B2 | 2/2009 | Yang |
| D591,106 S | 4/2009 | Dominique et al. |
| 7,520,872 B2 | 4/2009 | Biggie et al. |
| D593,801 S | 6/2009 | Wilson et al. |
| 7,588,560 B1 | 9/2009 | Dunlop |
| 7,682,347 B2 | 3/2010 | Parks et al. |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |

(56) References Cited

U.S. PATENT DOCUMENTS

| | | |
|---|---|---|
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns, Jr. et al. |
| 7,833,169 B2 | 11/2010 | Hannon |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,947,025 B2 | 5/2011 | Buglino et al. |
| 7,976,519 B2 | 7/2011 | Bubb et al. |
| 7,993,318 B2 | 8/2011 | Olsson et al. |
| 8,028,460 B2 | 10/2011 | Williams |
| 8,128,608 B2 | 3/2012 | Thevenin |
| 8,181,651 B2 | 5/2012 | Pinel |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| D676,241 S | 2/2013 | Merrill |
| 8,388,588 B2 | 3/2013 | Wada et al. |
| 8,425,482 B2 | 4/2013 | Khoubnazar |
| 8,546,639 B2 | 10/2013 | Wada et al. |
| 8,551,075 B2 | 10/2013 | Bengtson |
| 8,568,376 B2 | 10/2013 | Delattre et al. |
| 8,585,683 B2 | 11/2013 | Bengtson et al. |
| D704,330 S | 5/2014 | Cicatelli |
| D704,510 S | 5/2014 | Mason et al. |
| D705,423 S | 5/2014 | Walsh Cutler |
| 8,715,267 B2 | 5/2014 | Bengtson et al. |
| 8,864,730 B2 | 10/2014 | Conway et al. |
| 8,936,585 B2 | 1/2015 | Carson et al. |
| D729,581 S | 5/2015 | Boroski |
| 9,028,460 B2 | 5/2015 | Medeiros |
| 9,173,602 B2 | 11/2015 | Gilbert |
| 9,173,799 B2 | 11/2015 | Tanimoto et al. |
| 9,248,058 B2 | 2/2016 | Conway et al. |
| 9,480,595 B2 | 11/2016 | Baham et al. |
| D777,941 S | 1/2017 | Piramoon |
| D804,907 S | 12/2017 | Sandoval |
| D814,239 S | 4/2018 | Arora |
| 10,226,376 B2 | 3/2019 | Sanchez et al. |
| 10,335,121 B2 | 7/2019 | Desai |
| 10,376,406 B2 | 8/2019 | Newton |
| 10,390,989 B2 | 8/2019 | Sanchez et al. |
| 10,478,356 B2 | 11/2019 | Griffin |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0189992 A1 | 12/2002 | Schmidt et al. |
| 2003/0004436 A1 | 1/2003 | Schmidt et al. |
| 2003/0120178 A1 | 6/2003 | Heki |
| 2003/0181880 A1 | 9/2003 | Schwartz |
| 2003/0195484 A1 | 10/2003 | Harvie |
| 2003/0233079 A1 | 12/2003 | Parks et al. |
| 2004/0006321 A1 | 1/2004 | Cheng et al. |
| 2004/0127872 A1 | 7/2004 | Petryk et al. |
| 2004/0128749 A1 | 7/2004 | Scott |
| 2004/0143229 A1 | 7/2004 | Easter |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0254547 A1 | 12/2004 | Okabe et al. |
| 2005/0010182 A1 | 1/2005 | Parks et al. |
| 2005/0033248 A1 | 2/2005 | MacHida et al. |
| 2005/0070861 A1 | 3/2005 | Okabe et al. |
| 2005/0070862 A1 | 3/2005 | Tazoe et al. |
| 2005/0097662 A1 | 5/2005 | Leimkuhler et al. |
| 2005/0101924 A1 | 5/2005 | Elson et al. |
| 2005/0177070 A1 | 8/2005 | Levinson et al. |
| 2005/0197639 A1 | 9/2005 | Mombrinie |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0155214 A1 | 7/2006 | Wightman |
| 2006/0200102 A1 | 9/2006 | Cooper |
| 2006/0229576 A1 | 10/2006 | Conway et al. |
| 2006/0235359 A1 | 10/2006 | Marland |
| 2007/0006368 A1 | 1/2007 | Key et al. |
| 2007/0038194 A1 | 2/2007 | Wada et al. |
| 2007/0117880 A1 | 5/2007 | Elson et al. |
| 2007/0135786 A1 | 6/2007 | Schmidt et al. |
| 2007/0191804 A1 | 8/2007 | Coley |
| 2007/0214553 A1 | 9/2007 | Carromba et al. |
| 2007/0266486 A1 | 11/2007 | Ramirez |
| 2008/0004576 A1 | 1/2008 | Tanaka et al. |
| 2008/0015527 A1 | 1/2008 | House |
| 2008/0033386 A1 | 2/2008 | Okabe et al. |
| 2008/0091153 A1 | 4/2008 | Harvie |
| 2008/0091158 A1 | 4/2008 | Yang |
| 2008/0234642 A1 | 9/2008 | Patterson et al. |
| 2008/0281282 A1 | 11/2008 | Finger et al. |
| 2008/0287894 A1 | 11/2008 | Van Den Heuvel et al. |
| 2009/0025717 A1 | 1/2009 | Pinel |
| 2009/0056003 A1 | 3/2009 | Ivie et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0121289 A1 | 5/2010 | Parks et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028922 A1 | 2/2011 | Kay et al. |
| 2011/0034889 A1 | 2/2011 | Smith |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060300 A1 | 3/2011 | Weig et al. |
| 2011/0077495 A1 | 3/2011 | Gilbert |
| 2011/0172620 A1 | 7/2011 | Khambatta |
| 2011/0172625 A1 | 7/2011 | Wada et al. |
| 2011/0202024 A1 | 8/2011 | Cozzens |
| 2012/0035577 A1 | 2/2012 | Tomes et al. |
| 2012/0103347 A1 | 5/2012 | Wheaton et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0330256 A1 | 12/2012 | Wilcox et al. |
| 2013/0006206 A1 | 1/2013 | Wada et al. |
| 2013/0053804 A1 | 2/2013 | Soerensen et al. |
| 2013/0096523 A1 | 4/2013 | Chang et al. |
| 2014/0031774 A1 | 1/2014 | Bengtson |
| 2014/0157499 A1 | 6/2014 | Suzuki et al. |
| 2014/0182051 A1 | 7/2014 | Tanimoto et al. |
| 2014/0196189 A1 | 7/2014 | Lee et al. |
| 2014/0348139 A1 | 11/2014 | Gomez Martinez |
| 2014/0371628 A1 | 12/2014 | Desai |
| 2015/0047114 A1 | 2/2015 | Ramirez |
| 2015/0135423 A1 | 5/2015 | Sharpe et al. |

(56) References Cited

U.S. PATENT DOCUMENTS

| | | | |
|---|---|---|---|
| 2015/0157300 A1 | 6/2015 | Ealovega et al. |
| 2015/0209194 A1 | 7/2015 | Heyman |
| 2015/0359660 A1 | 12/2015 | Harvie |
| 2015/0366699 A1 | 12/2015 | Nelson |
| 2016/0029998 A1 | 2/2016 | Brister et al. |
| 2016/0058322 A1 | 3/2016 | Brister et al. |
| 2016/0100976 A1 | 4/2016 | Conway et al. |
| 2016/0106604 A1 | 4/2016 | Timm |
| 2016/0278662 A1 | 9/2016 | Brister et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0143534 A1 | 5/2017 | Sanchez |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252202 A9 | 9/2017 | Sanchez et al. |
| 2017/0266031 A1 | 9/2017 | Sanchez et al. |
| 2017/0312116 A1 | 11/2017 | Laniado |
| 2017/0333244 A1 | 11/2017 | Laniado |
| 2017/0042748 A1 | 12/2017 | Griffin |
| 2017/0348139 A1 | 12/2017 | Newton et al. |
| 2018/0008451 A1 | 1/2018 | Stroebech |
| 2018/0008804 A1 | 1/2018 | Laniado |
| 2018/0028349 A1 | 2/2018 | Newton et al. |
| 2018/0049910 A1 | 2/2018 | Newton |
| 2018/0064572 A1 | 3/2018 | Wiltshire |
| 2018/0200101 A1 | 7/2018 | Su |
| 2018/0228642 A1 | 8/2018 | Davis et al. |
| 2019/0038451 A1 | 2/2019 | Harvie |
| 2019/0142624 A1 | 5/2019 | Sanchez et al. |
| 2019/0224036 A1 | 7/2019 | Sanchez et al. |
| 2019/0314190 A1 | 10/2019 | Sanchez et al. |
| 2020/0046544 A1 | 2/2020 | Godinez et al. |
| 2020/0085610 A1 | 3/2020 | Cohn et al. |

FOREIGN PATENT DOCUMENTS

| | | |
|---|---|---|
| CN | 1720888 A | 1/2006 |
| CN | 101262836 A | 9/2008 |
| CN | 103717180 A | 4/2014 |
| CN | 107847384 A | 3/2018 |
| DE | 9107554.9 U1 | 5/1995 |
| DE | 4443710 A1 | 6/1995 |
| DE | 102011103783 A1 | 12/2012 |
| DK | 9600118 | 11/1996 |
| EP | 0032138 A2 | 7/1981 |
| EP | 0066070 B1 | 12/1982 |
| EP | 0119143 B1 | 11/1988 |
| EP | 0610638 A1 | 8/1994 |
| EP | 0613355 A1 | 9/1994 |
| EP | 1382318 A1 | 1/2004 |
| EP | 1382318 B1 | 5/2006 |
| EP | 2180907 A1 | 5/2010 |
| EP | 2380532 A1 | 10/2011 |
| EP | 2879534 B1 | 3/2017 |
| EP | 3169292 61 | 11/2019 |
| GB | 1467144 A | 3/1977 |
| GB | 2106395 A | 4/1983 |
| GB | 2148126 B | 7/1987 |
| GB | 2191095 A | 12/1987 |
| GB | 2199750 A | 7/1988 |
| GB | 2260907 A | 5/1993 |
| GB | 2469496 A | 10/2010 |
| JP | S5410596 A | 1/1979 |
| JP | S5410596 Y2 | 5/1979 |
| JP | H0267530 A | 3/1990 |
| JP | H02103871 A | 4/1990 |
| JP | H0460220 A | 2/1992 |
| JP | H05123349 A | 5/1993 |
| JP | H11113946 A | 4/1999 |
| JP | H11290365 A | 10/1999 |
| JP | 2000185068 A | 7/2000 |
| JP | 3087938 | 9/2000 |
| JP | 2001054531 | 2/2001 |
| JP | 2001054531 A | 2/2001 |
| JP | 2001276107 A | 10/2001 |
| JP | 2001276108 A | 10/2001 |
| JP | 2004267530 A | 9/2004 |
| JP | 2005066325 A | 3/2005 |
| JP | 2006026108 A | 2/2006 |
| JP | 3123547 B2 | 6/2006 |
| JP | 2006204868 A | 8/2006 |
| JP | 3132659 B2 | 5/2007 |
| JP | 4039641 B2 | 11/2007 |
| JP | 4747166 B2 | 5/2011 |
| JP | 2012523869 A | 10/2012 |
| JP | 2015092945 A | 5/2015 |
| JP | 3198994 B2 | 7/2015 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9309736 A2 | 5/1993 |
| WO | 9309736 A3 | 6/1993 |
| WO | 9600096 A1 | 1/1996 |
| WO | 0057784 A1 | 10/2000 |
| WO | 0145618 A1 | 6/2001 |
| WO | 0145621 A1 | 6/2001 |
| WO | 03071931 A2 | 9/2003 |
| WO | 03071931 A3 | 2/2004 |
| WO | 2004019836 A1 | 3/2004 |
| WO | 2005089687 A2 | 9/2005 |
| WO | 2005107661 A2 | 11/2005 |
| WO | 2007007845 A1 | 1/2007 |
| WO | 2007042823 A2 | 4/2007 |
| WO | 2008078117 A1 | 7/2008 |
| WO | 2009052496 A1 | 4/2009 |
| WO | 2009101738 A1 | 8/2009 |
| WO | 2010030122 A3 | 7/2010 |
| WO | 2011024864 A1 | 3/2011 |
| WO | 2011132043 A1 | 10/2011 |
| WO | 2013103291 A2 | 7/2013 |
| WO | 2013131109 A1 | 9/2013 |
| WO | 2014041534 A1 | 3/2014 |
| WO | 2015023599 A1 | 2/2015 |
| WO | 2015169403 A1 | 11/2015 |
| WO | 2015170307 A1 | 11/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016200088 A1 | 12/2016 |
| WO | 2017209779 A1 | 12/2017 |
| WO | 2017210524 A1 | 12/2017 |
| WO | 2018022414 A1 | 2/2018 |
| WO | 2018056953 A1 | 3/2018 |
| WO | 2018138513 A1 | 8/2018 |
| WO | 2018235065 A1 | 12/2018 |

OTHER PUBLICATIONS

AMXDmax In-Flight Bladder Relief; Omni Medical 2015; Omni Medical Systems, Inc.

Office Action for U.S. Appl. No. 14/947,759, dated Mar. 17, 2006.

Final Office Action for U.S. Appl. No. 14/947,759, dated Apr. 8, 2016.

U.S. Appl. No. 14/952,591, filed Nov. 25, 2015.

Final Office Action for U.S. Appl. No. 14/947,759, dated Apr. 8, 2016 (8 pages).

International Search Report and Written Opinion for International Patent Application No. PCT/US16/49274, dated Dec. 1, 2016 (11 pages).

International Search Report and Written Opinion of the International Searching Authority for International Patent Application No. PCT/US2017/035625, dated Aug. 15, 2017 (17 pages).

Non-Final Office Action for U.S. Appl. No. 14/952,591 dated Aug. 1, 2017.

(56) References Cited

OTHER PUBLICATIONS

Non-Final Office Action for U.S. Appl. No. 14/947,759, dated Mar. 17, 2016 (7 pages).
U.S. Appl. No. 15/171,968, filed Jun. 2, 2016.
Parmar,"10 Finalists Chosen for Dare-to-Dream Medtech Design Challenge (PUreWick)," Design Services, Nov. 10, 2014 (3 pages).
Purewick,"Incontinence Relief for Women" Presentation, (7 pages), Sep. 23, 2015.
Pytlik,"Super Absorbent Polymers," University of Buffalo http://www.courses.sens.buffalo.edu/ce435/Diapers/Diapers.html, accessed on Feb. 17, 2017.
Advisory Action for U.S. Appl. No. 14/952,591 dated Jun. 1, 2018.
Corrected International Search Report and Written Opinion for International Application No., PCT/US2017/043025 dated Jan. 11, 2018.
Final Office Action for U.S. Appl. No. 14/952,591 dated Feb. 23, 2018.
International Search Report and Written Opinion for International Application No. PCT/US2017/043025 dated Oct. 18, 2017.
International Search Report and Written Opinion for International Application No. PCT/US2018/015968 dated Apr. 6, 2018.
Non-Final Office Action for U.S. Appl. No. 14/952,591 dated Sep. 28, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Jul. 13, 2018.
Non-Final Office Action for U.S. Appl. No. 15/611,587 dated Dec. 29, 2017.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
"Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
"Step by Step How Ur24 WorksHome", http://medicalpatentur24.com, last accessed Dec. 6, 2017, Aug. 30, 2017, 4 pages.
Advisory Action for U.S. Appl. No. 15/238,427 dated Apr. 10, 2019.
Corrected Notice of Allowability for U.S. Appl. No. 15/221,106 dated Jul. 2, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Issue Notification for U.S. Appl. No. 15/611,587 dated Feb. 20, 2019.
Non-Final Office Action for U.S. Appl. No. 14/952,591 dated Mar. 21, 2019.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
U.S. Appl. No. 15/221,106, filed Jul. 27, 2016.
U.S. Appl. No. 16/369,676, filed Mar. 29, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
Final Office Action for U.S. Appl. No. 14/952,591, dated Nov. 1, 2019.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Non-Final Office Action for U.S. Appl. No. 29/624,661 dated Jul. 18, 2019.
Defendant and Counterclaim Plaintiff Sage Products, LLC's Answer, Defenses, and Counterclaims to Plaintiff's Amended Complaint, Nov. 1, 2019.
Advisory Action for U.S. Appl. No. 14/722,613 dated Mar. 4, 2019.
Final Office Action for U.S. Appl. No. 14/722,613 dated Nov. 29, 2018.
Final Office Action for U.S. Appl. No. 29/624,661 dated Feb. 18, 2020.
Non-Final Office Action for U.S. Appl. No. 14/592,591 dated Mar. 20, 2020.
Non-Final Office Action for U.S. Appl. No. 14/722,613 dated Jun. 13, 2019.
Non-Final Office Action for U.S. Appl. No. 15/612,325 dated Mar. 19, 2020.
U.S. Appl. No. 16/433,773, filed Jun. 6, 2019.
U.S. Appl. No. 16/478,180, filed Jul. 16, 2019.
U.S. Appl. No. 62/452,437, filed Jan. 31, 2017.
U.S. Appl. No. 62/994,912, filed Mar. 26, 2020.
Final Office Action for U.S. Appl. No. 14/952,591 dated Nov. 27, 2020.
Final Office Action for U.S. Appl. No. 15/612,325 dated Sep. 17, 2020.
Non-Final Office Action for U.S. Appl. No. 15/171,968 dated May 11, 2020.
Non-Final Office Action for U.S. Appl. No. 16/899,956 dated Oct. 16, 2020.
Non-Final Office Action for U.S. Appl. No. 16/904,868 dated Nov. 25, 2020.
Non-Final Office Action for U.S. Appl. No. 16/905,400 dated Dec. 2, 2020.
Non-Final Office Action for U.S. Appl. No. 17/088,272 dated Jan. 25, 2021.
Non-Final Office Action for U.S. Appl. No. 29/694,002 dated Jun. 24, 2020.
Notice of Allowance for U.S. Appl. No. 15/612,325 dated Jan. 21, 2021.
Notice of Allowance for U.S. Appl. No. 29/624,661 dated Jul. 10, 2020.
Notice of Allowance for U.S. Appl. No. 29/624,661 dated May 14, 2020.
Notice of Allowance for U.S. Appl. No. 29/624,661 dated Sep. 29, 2020.
Notice of Allowance for U.S. Appl. No. 29/694,002 dated Jan. 29, 2021.

(56) References Cited

OTHER PUBLICATIONS

Notice of Allowance for U.S. Appl. No. 29/694,002 dated Oct. 16, 2020.
U.S. Appl. No. 16/904,868 filed Jun. 18, 2020.
U.S. Appl. No. 16/905,400 filed Jun. 18, 2020.
U.S. Appl. No. 17/051,550 filed Oct. 29, 2020.
U.S. Appl. No. 17/051,554 filed Oct. 29, 2020.
U.S. Appl. No. 17/051,585 filed Oct. 29, 2020.
U.S. Appl. No. 17/051,600 filed Oct. 29, 2020.
U.S. Appl. No. 17/088,272 filed Nov. 3, 2020.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. No's 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Excerpts from the 508 (U.S. Pat. No. 8,278,508) Patent's Prosecution History, 2020, 99 pages.
Plaintiff's Opening Claim Construction Brief, Case No. 19/1508-MN, Oct. 16, 2020, 26 pages.
Plaintiff's Identification of Claim Terms and Proposed Constructions, Case No. 19/1508-MN, 3 pages.
PureWick's Response to Interrogatory No. 9 in *PureWick, LLC* v. *Sage Products, LLC*, Case No. 19/1508-MN, Mar. 23, 2020, 6 pages.
Sage's Preliminary Identification of Claim Elements and Proposed Constructions for U.S. Pat. No. 8,287,508, 10,226,376, 10,390,989 and 10,376,407, Case No. 19/1508-MN, 7 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDX—Advanced Mission Extender Device Brochure", Omni Medical, Omni Brochure—http://www.omnimedicalsys.com/uploads/AMXDFixedWing.pdf, 2 pages.
"How Period Panties Work", www.shethinx.com/pages/thinx-itworks, 2020, 10 pages.
"In Flight Bladder Relief", Omni Medical, Omni Presentation https://www.omnimedicalsys.com/uploads/AMXDmax_HSD.pdf, 14 pages.
"Research and Development Work Relating to Assistive Technology Jun. 2005", British Department of Health, Nov. 2006, 40 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Sachtman, "New Relief for Pilots? It Depends", Wired, https://www.wired.com/2008/05/pilot-relief/, 2008, 2 pages.

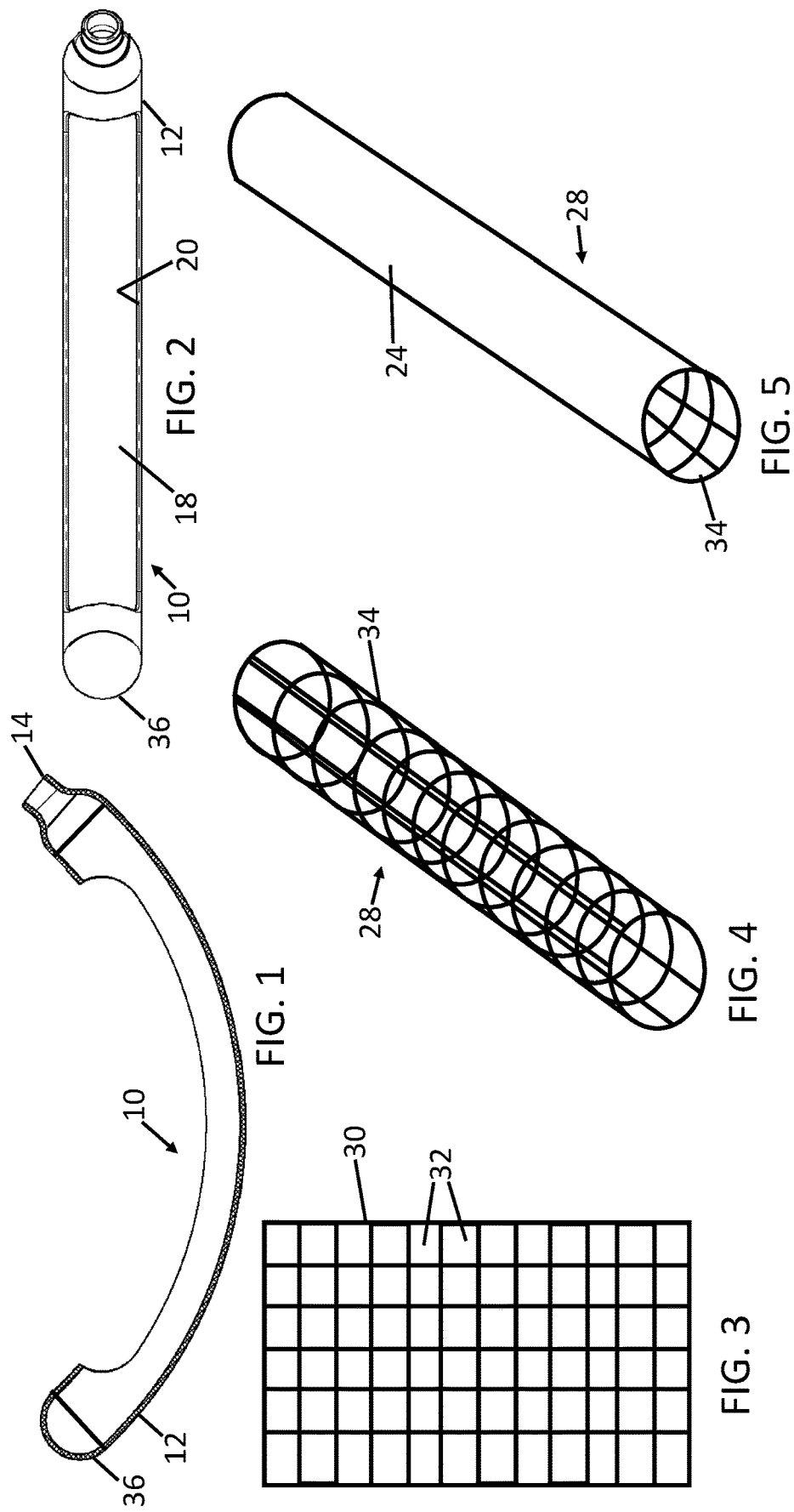

USING WICKING MATERIAL TO COLLECT LIQUID FOR TRANSPORT

BACKGROUND OF THE INVENTION

The invention generally pertains to using wicking material to collect liquid for transport and is particularly directed to a container that can be used to so collect a liquid, such as urine, from the body of a person or an animal in such a manner that the liquid can be readily transported from the container as the liquid is being collected, and is also directed to a wicking material applicator for use with such a container.

A container for collecting urine and transporting the collected urine voided from a person's body is described in U.S. Pat. No. 8,287,508 to Robert A. Sanchez. The container described in said patent is made of plastic or some other material and defines a chamber for collecting urine. The container is closed, except for having an array of openings through which urine can be drawn into the chamber for collection and at least one outlet port through which urine can be drawn away from the chamber by a transport tube inserted into the chamber. The exterior of the container is configured for enabling a moisture-wicking article to be secured over the array of openings and for enabling the secured moisture-wicking article to be disposed in contact with the region of a female body surrounding the urethral opening. A vacuum pump is attached to the transport tube in order to create a partial vacuum in the chamber in order to draw urine into the chamber for collection of the urine and in order to draw the collected urine away from the chamber.

SUMMARY OF THE INVENTION

The invention provides a container for collecting liquid for transport, comprising: a shell having a port adapted for receiving tubing and configured to define a chamber that has a window in an exterior surface of the shell, with the window being so positioned that when a wicking material, which is adapted to be applied against a particular source of moisture and which is so dimensioned that when the wicking material is received within the shell and applied through the window to the particular source of moisture, the shell is at least partially closed so that when tubing is inserted through the port into the shell chamber and the shell is otherwise closed a partial vacuum can be created within the shell chamber to draw moisture into the shell chamber through the wicking material for collection as a liquid within the shell chamber for transport from the shell chamber via the tubing.

In one aspect of the invention, the above-described container is combined with a wicking material applicator that is adapted for so supporting the wicking material that the wicking material can be received within the shell and applied through the window against the particular source of moisture.

The invention also provides a wicking material applicator for use with a container for collecting liquid for transport that comprises: a shell having a port adapted for receiving tubing and configured to define a chamber that has a window in an exterior surface of the shell, with the window being so positioned that when a wicking material, which is adapted to be applied against a particular source of moisture and which is so dimensioned that when the wicking material is received within the shell and applied through the window to the particular source of moisture, the shell is at least partially closed so that when tubing is inserted through the port into the shell chamber and the shell is otherwise closed a partial vacuum can be created within the shell chamber to draw moisture into the shell chamber through the wicking material for collection as a liquid within the shell chamber for transport from the shell chamber via the tubing, wherein the wicking material applicator is adapted for so supporting the wicking material that the wicking material can be received within the shell and applied through the window against the particular source of moisture The invention provides an improved container and an improved wicking material applicator that are particularly configured and adapted for applying the wicking material against a particular source of moisture.

The invention is particularly useful for persons or animals during various circumstances. These circumstances include a condition such as incontinence or a disability that limits or impairs mobility. These circumstances also include restricted travel conditions, such as sometimes experienced by pilots, drivers, workers in hazardous areas, etc. These circumstances further include collection of urine for monitoring purposes or clinical testing.

Additional features of the invention are described with reference to the detailed description.

BRIEF DESCRIPTION OF THE DRAWING

FIG. 1 is a side view of an exemplary embodiment of a container according to the invention.

FIG. 2 is a top view of the embodiment of the container shown in FIG. 1

FIG. 3 is a view of an exemplary embodiment of a sheet of material having openings included in an exemplary embodiment of a wicking material applicator according to the invention.

FIG. 4 is a view of the exemplary embodiment of a wicking material applicator according to the invention FIG. 5 is a view of the wicking material applicator shown in FIG. 4 with wicking material disposed about the applicator.

DETAILED DESCRIPTION

Referring to FIG. 1, an exemplary embodiment of a container 10 according to the invention includes a shell 12 having a port 14 that is adapted for receiving tubing (not shown). The shell 12 is configured to define a chamber 18 that has a window 20 in an exterior surface of the shell 12.

The window 20 is so positioned that when a wicking material 24, which is adapted to be applied against a particular source of moisture (not shown), and which is so dimensioned that when the wicking material 24 is received within the shell 12 and applied through the window 20 to the particular source of moisture, the shell 12 is at least partially closed so that when tubing is inserted through the port 14 into the shell chamber 18 and the shell 12 is otherwise closed a partial vacuum can be created within the shell chamber 18 to draw moisture into the shell chamber 18 through the wicking material 24 for collection as a liquid within the shell chamber 18 for transport from the shell chamber 18 via the tubing.

In a preferred exemplary embodiment, the shell 12 is made of a compliant impermeable plastic material, such as silicone.

In a preferred exemplary embodiment, the portion of the shell 12 adjacent the window 20 is arched so that the wicking material can be better applied against the region of a female body surrounding the urethral opening.

An exemplary embodiment of a wicking material applicator 28 is described with reference to FIGS. 3, 4 and 5. The applicator 28 includes material having symmetrical or non-symmetrical openings and formed to define an extended hollow framework about which the wicking material can be, or is, disposed. In the exemplary embodiment shown in FIG. 5, material 30, such as porous spun plastic or plastic netting material, having openings 32, as shown in FIG. 3, is formed to define an extended hollow framework 34, as shown in FIG. 4, about which framework 34 wicking material 24 can be, or is, disposed, as shown in FIG. 5. Preferably, the material 30 is flexible polypropylene. In other embodiments, the material is nylon, polyester, some other plastic or a natural material.

Because the preferred framework 34 is flexible, the wicking material applicator 28 is compliant and is dimensioned accordingly to fit snuggly within the shell chamber 18 so that the wicking material can be pressed through the window 20 against the particular source of moisture.

An exemplary method of assembling a wicking material applicator 28 within the chamber 18 of the shell includes the steps of:

(a) disposing a wicking material 24, such as tubular gauze, about a hollow plastic pipe (not shown);

(b) inserting the pipe bearing the wicking material 24 into the shell chamber 18 through the port 14 in one end of the shell whereupon the wicking material 24 is positioned so that the wicking material 24 can be applied through the window 20 against a particular source of moisture;

(c) forming a wicking material applicator 28 from material having symmetrical or non-symmetrical openings to define the extended hollow framework 34 that is shown in FIG. 4;

(d) inserting the extended hollow framework 34 through the pipe so that the framework 34 is coextensive with the wicking material 24; and (e) removing the pipe from the shell chamber 18 while simultaneously grasping both the wicking material 24 and the extended hollow framework so that the wicking material 24 is disposed about the extended hollow framework 34 to provide an assembled a wicking material applicator 28 that is so positioned that the wicking material 24 can be applied through the window 20 against a particular source of moisture.

Alternatively, the wicking material applicator 28 is assembled outside of the shell chamber 18 and is then positioned within the shell chamber by inserting the applicator 28 through the window 20 and flexing the shell 12 around and over the sides of the wicking material applicator 28.

Preferably, the method of assembling the applicator 28 outside the shell chamber 18 includes the steps of (a) disposing a wicking material 24, such as tubular gauze, about a hollow plastic pipe (not shown);

(b) flexing a sheet of the flexible material 30 to define the extended hollow framework 34 that is shown in FIG. 4;

(c) inserting the extended hollow framework 34 through the pipe so that the framework 34 is coextensive with the wicking material 24;

(d) removing the pipe while simultaneously grasping both the wicking material 24 and the extended hollow framework 34 so that the wicking material 24 is disposed about the extended hollow framework 34; and (e) while the wicking material 24 is disposed about the extended hollow framework 34, cutting a section of the so-disposed wicking material 24 to the desired length to thereby provide an assembled a wicking material applicator 28.

In an alternative method of assembling the applicator 28 outside the shell chamber 18, wicking material such as rolled gauze is applied to a sheet of material having openings and attached thereto with an adhesive or by compression of a frame around the perimeter of the sheet. Assembly of the wicking material applicator is then completed by shaping the sheet having the wicking material applied thereto into an extended hollow framework and maintaining the shape of extended hollow framework with adhesive or adhesive tape. Alternatively, the shape of the extended hollow framework is maintained due to compression when inserted into the shell 12.

Different embodiments of a container for a urine collection device according to the invention are configured for use by both adult and pediatric applications, and for veterinary applications involving animals of different species and sizes.

The benefits specifically stated herein do not necessarily apply to every conceivable embodiment of the present invention. Further, such stated benefits of the present invention are only examples and should not be construed as the only benefits of the present invention.

While the above description contains much specificity, these specifics are not to be construed as limitations on the scope of the present invention, but rather as examples of the embodiments described herein. Other variations are possible and the scope of the present invention should be determined not by the embodiments described herein but rather by the claims and their legal equivalents.

The invention claimed is:

1. A container for collecting liquid for transport, the container comprising:

a generally cylindrical shell shaped to receive a generally cylindrical wicking material applicator and having a port in a first end adapted for receiving tubing, a second end distal to the first end, a back surface extending between the first end and the second end, and a front surface distal to at least a portion of the back surface, the shell defining a chamber and having two elongated edges spaced inwardly from the front surface that at least partially define an elongated window opening in the front surface of the shell, wherein the shell is shaped and defines the window opening positioned on the front surface of the shell such that when the generally cylindrical wicking material applicator is received within the shell:

the shell includes a compliant material configurable to form an arched position that supports a wicking material on an arched outer surface of the generally cylindrical wicking material applicator against a particular source of moisture through the window opening, the arched position of the shell forming an arch that extends at least partially between the first end and the second end; and the shell is at least partially closed so that when tubing is inserted through the port into the chamber, the shell is otherwise closed and a partial vacuum is created within the chamber when a vacuum pump coupled to the tubing is activated to draw moisture into the chamber through the tubular wicking material for collection as a liquid within the chamber for transport from the chamber via the tubing.

2. The container according to claim 1, further comprising the generally cylindrical wicking material applicator configured to support the wicking material when the wicking material is received within the shell and applied through the window opening against the particular source of moisture.

3. The container according to claim 2, wherein the generally cylindrical wicking material applicator comprises a material having symmetrical or non-symmetrical openings and formed to define an extended hollow framework about which the wicking material is disposed.

4. The container according to claim 1, wherein the shell is an impermeable material.

5. A wicking material applicator for use with a container for collecting liquid for transport that comprises a shell configurable to an arched position and having a port adapted for receiving tubing, the shell defining a chamber and a window opening defined at least partially by two elongated edges spaced inwardly from a front surface of the shell, the wicking material applicator comprising:
 a cylindrical hollow support formed from a porous material; and
 a wicking material in a tubular shape disposed about the hollow support wherein a portion of the wicking material in the tubular shape forms an arched surface that is adapted to be applied against a particular source of moisture through the window opening when the wicking material applicator is positioned within the shell and the shell is in the arched position, wherein the wicking material applicator is so dimensioned that when the wicking material applicator is received within the shell and applied through the window opening to the particular source of moisture, the arched surface is spaced outwardly from the two elongated edges defining the window opening and the shell is at least partially closed so that when tubing is inserted through the port into the chamber, the shell is otherwise closed, and a vacuum pump coupled to the tubing is activated, a partial vacuum is created within the chamber to draw moisture into the chamber through the wicking material for collection as a liquid within the chamber for transport from the chamber via the tubing, wherein the support is adapted for so supporting the wicking material that the wicking material can be received within the shell and applied through the window opening against the particular source of moisture.

6. The wicking material applicator according to claim 5, wherein the hollow support comprises material having symmetrical or non-symmetrical openings and formed to define an extended hollow framework about which the wicking material is disposed.

7. The wicking material applicator according to claim 6, wherein the material defining the framework comprises a sheet of flexible plastic material formed to define said extended hollow framework about which the wicking material is disposed.

8. The wicking material applicator according to claim 6, wherein the material defining the framework comprises spun plastic formed to define the extended hollow framework about which the wicking material is disposed.

9. The wicking material applicator according to claim 5, wherein the hollow support comprises natural material having openings that allow fluid to flow through and formed to define an extended hollow framework about which the wicking material is disposed.

10. The container of claim 4, wherein the shell includes silicone.

11. A system for collecting liquid for transport, the system comprising:
 a shell defining a chamber and a window opening, the shell having a first end including a port configured to receive tubing, a second end distal to the first end, a back surface extending between the first end and the second end, a front surface distal to the back surface, two elongated edges spaced inwardly from the front surface that at least partially define the window opening in the front surface, and a compliant material configurable to form an arched position that includes an arch extending at least partially between the first end and the second end; and
 a generally cylindrical wicking material applicator positioned within the chamber and including:
  a hollow support formed form a porous material; and
  a wicking material in a tubular shape disposed about the hollow support;
 wherein the window opening is sized such that the shell in the arched position supports an arched portion of the wicking material in the tubular shape exposed through the window opening for application against a particular source of moisture.

12. The system of claim 11, wherein when the wicking material is positioned within the chamber, tubing is inserted through the port into the chamber the shell is otherwise closed, and a vacuum pump coupled to the tubing is activated, a partial vacuum is created within the chamber to draw moisture into the chamber through the portion of the wicking material for collection as a liquid within the chamber for transport from the chamber via the tubing.

13. The system of claim 11, wherein the shell includes an impermeable material.

14. The system of claim 13, wherein the shell includes an impermeable silicone.

15. The system of claim 11, wherein the hollow support includes porous material formed to define an extended hollow framework.

16. The system of claim 11, wherein:
 the shell has two elongated edges and two arched edges extending between the two longitudinal edges that define the window; and
 the shell and the wicking material applicator are sized such that the wicking material is fitted against the two arched edges and the arched portion of the wicking material in the tubular shape is exposed through the window opening for application against a particular source of moisture.

17. The system of claim 11, wherein the shell flexes around the wicking material applicator.

\* \* \* \* \*